United States Patent

Davis

[11] Patent Number: 5,217,442
[45] Date of Patent: Jun. 8, 1993

[54] ASPIRATION AND REFILL KIT FOR A MEDICATION INFUSION PUMP

[75] Inventor: Mark W. Davis, Newbury Park, Calif.

[73] Assignee: MiniMed Technologies, Sylmar, Calif.

[21] Appl. No.: 590,640

[22] Filed: Sep. 28, 1990

[51] Int. Cl.[5] .................................. A61M 31/00
[52] U.S. Cl. ................................ 604/285; 604/191; 604/164; 604/208; 604/21 D; 604/218; 604/248
[58] Field of Search ............... 604/220, 236, 121, 248, 604/208, 211, 218, 207, 210, 191, 164, 285, 890.1, 890.2, 890.3, 187, 246, 248, 158, 161

[56] References Cited

U.S. PATENT DOCUMENTS

| | | | |
|---|---|---|---|
| 32,826 | 7/1881 | Bonchek et al. | 604/121 |
| 1,410,530 | 3/1922 | Larche | 604/231 |
| 2,489,040 | 11/1946 | Lawshe | 604/220 |
| 2,875,761 | 1/1948 | Teves | 604/164 |
| 3,143,109 | 8/1964 | Gewertz | 604/236 |
| 3,577,980 | 5/1971 | Cohen | 128/2 |
| 3,747,812 | 7/1973 | Karman et al. | 222/387 |
| 4,036,232 | 7/1977 | Genese | 128/278 |
| 4,187,849 | 2/1980 | Stim | 128/278 |
| 4,386,606 | 6/1983 | Tretinyak et al. | 604/220 |
| 4,562,844 | 1/1986 | Carpenter et al. | 128/675 |
| 4,592,746 | 6/1986 | Burkholder et al. | 604/220 |
| 4,661,097 | 4/1987 | Fischell et al. | 604/123 |
| 4,673,394 | 6/1987 | Fenton, Jr. et al. | 604/236 |
| 4,721,506 | 3/1989 | Helmer et al. | 604/210 |
| 4,758,232 | 7/1988 | Chak | 604/220 |
| 4,790,331 | 12/1988 | Okada et al. | 604/53 |

FOREIGN PATENT DOCUMENTS

| | | | |
|---|---|---|---|
| 0032826 | 7/1981 | European Pat. Off. | 604/121 |
| 0881415 | 4/1943 | France | 604/214 |

Primary Examiner—David Isabella
Assistant Examiner—R. Clarke
Attorney, Agent, or Firm—Leslie S. Miller

[57] ABSTRACT

A kit is provided for use in refilling a medication infusion pump of the type adapted for implantation into the body of a patient. The kit comprises a syringe having a plunger mounted for reciprocation within a syringe barrel having a manually operable control valve mounted at a nose end thereof. The syringe further includes a lock for retaining the plunger subsequent to retraction motion with the control valve closed to pull and maintain a vacuum within the syringe barrel. With this construction, the syringe can be connected transcutaneously with a medication reservoir within an implanted infusion pump to aspirate residual medication from the pump. Alternately, the syringe can be used to degas medication within the barrel preparatory to transcutaneous delivery to the pump reservoir. In either case, the syringe is designed for facilitated and safe manipulation to permit rapid pump aspiration and refill at periodic intervals according to patient requirements.

22 Claims, 7 Drawing Sheets

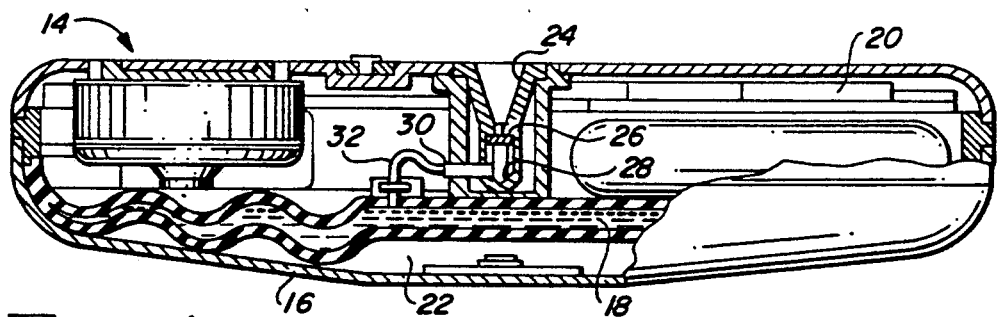
FIG. 4
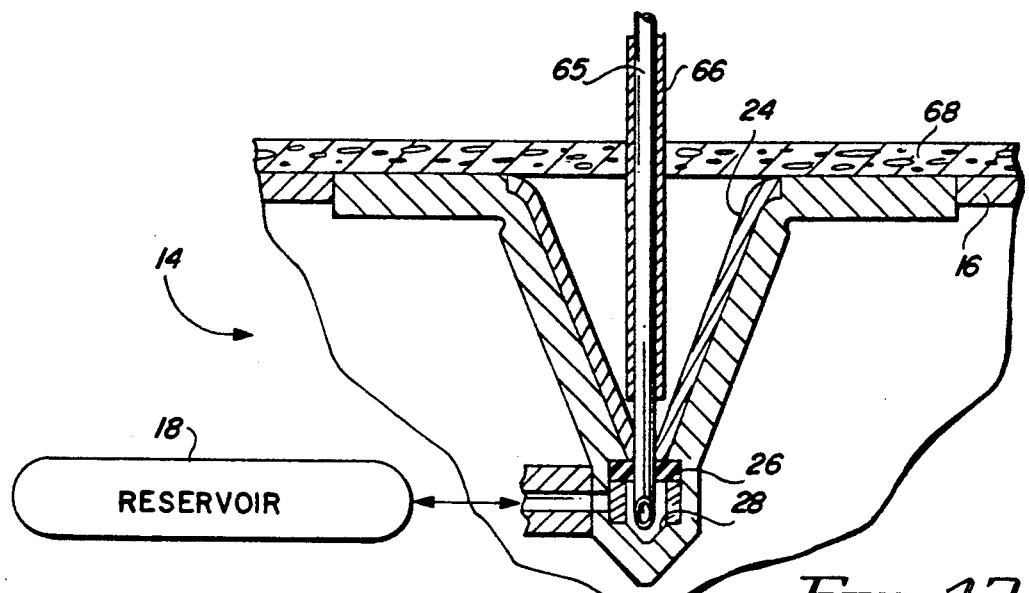
FIG. 12
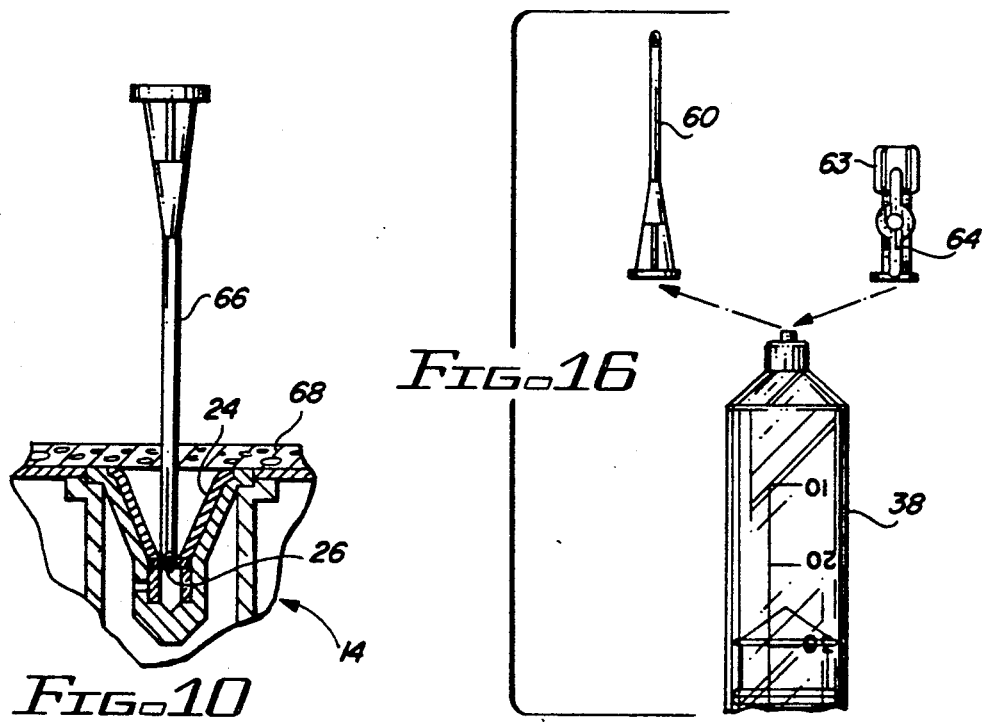
FIG. 10
FIG. 16

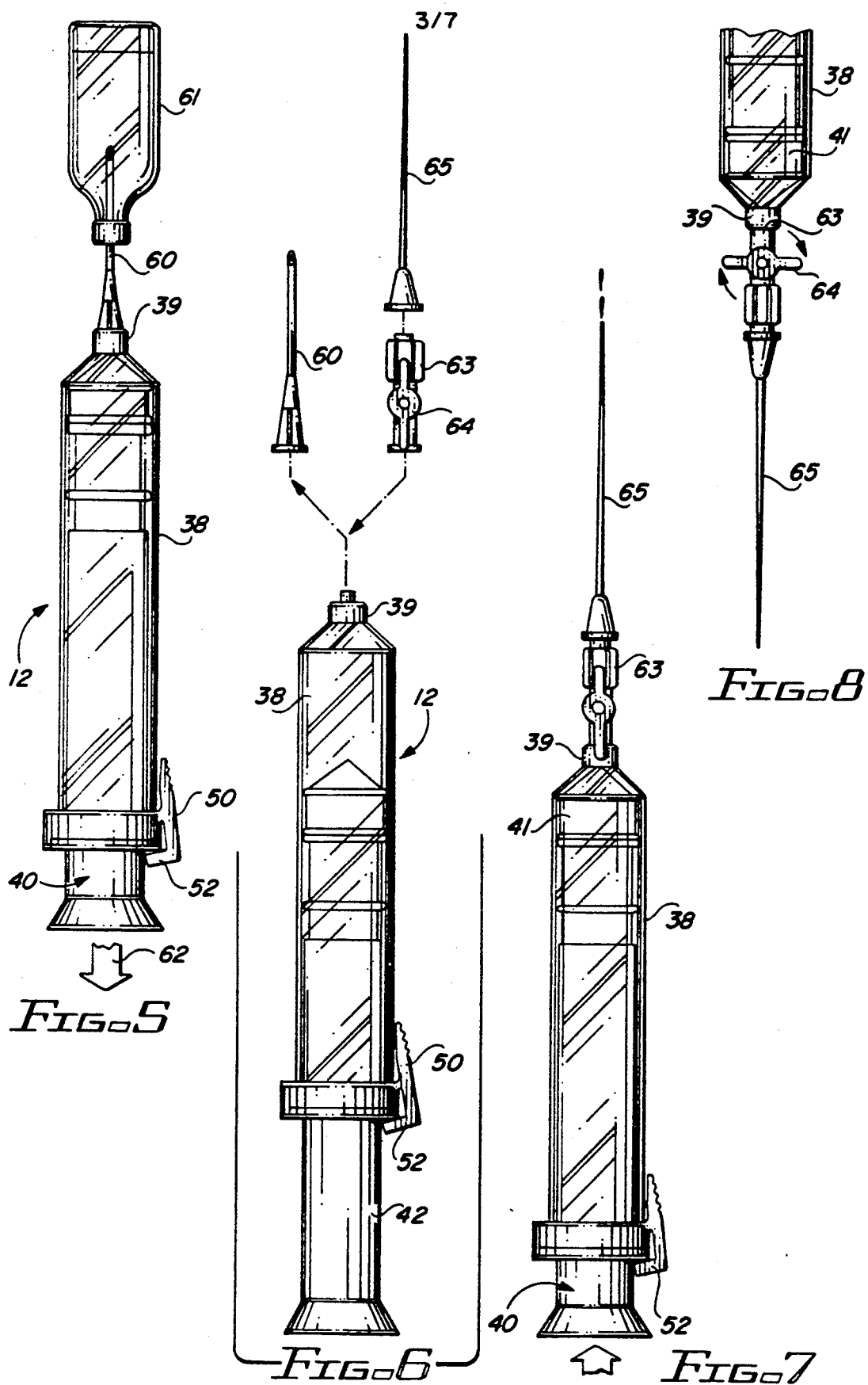

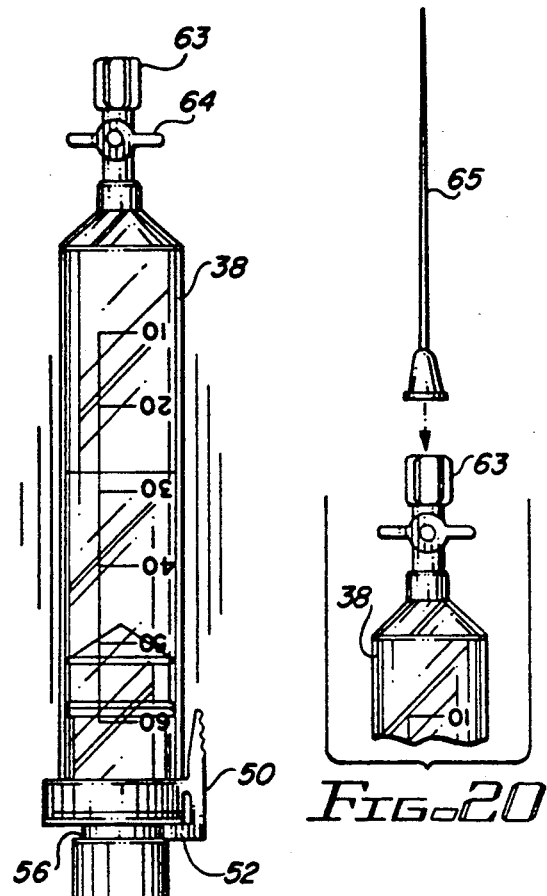
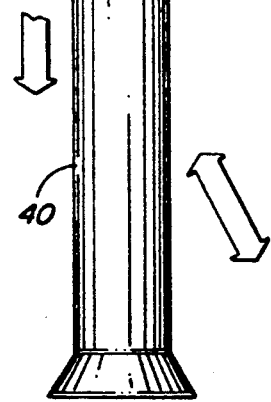
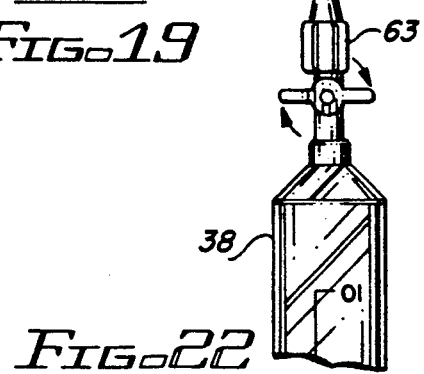
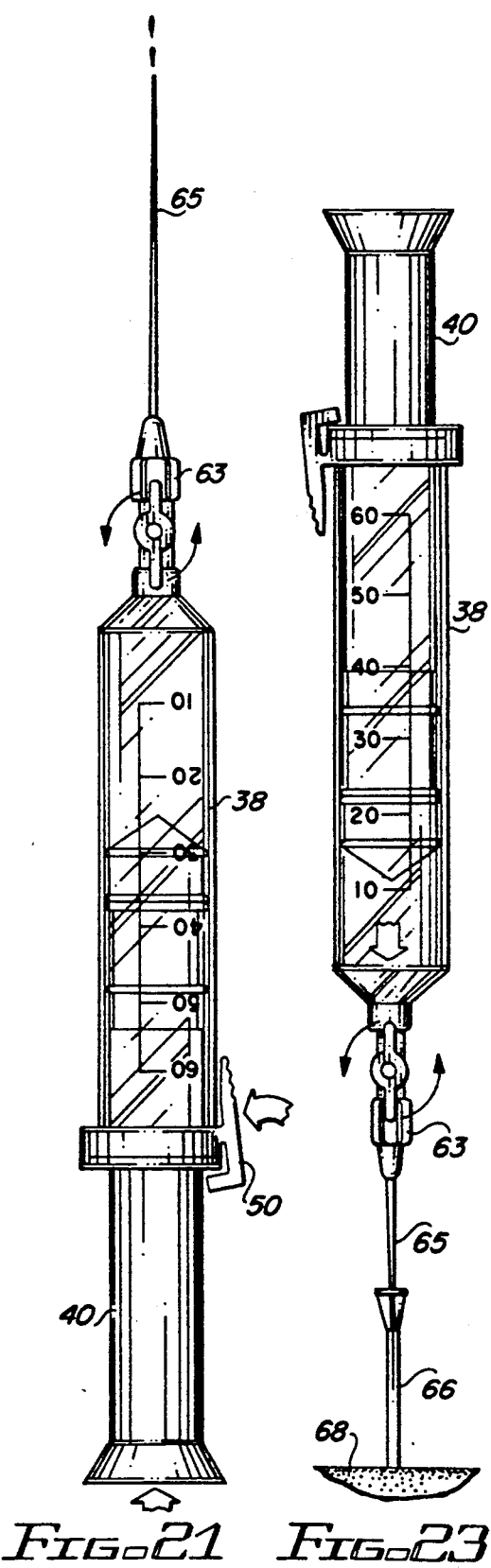
FIG.-19  FIG.-20  FIG.-22  FIG.-21  FIG.-23

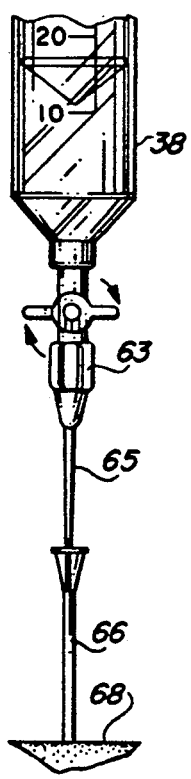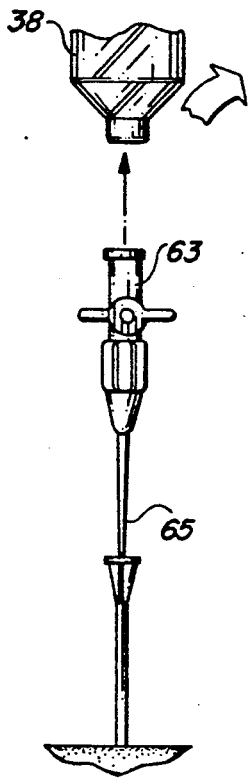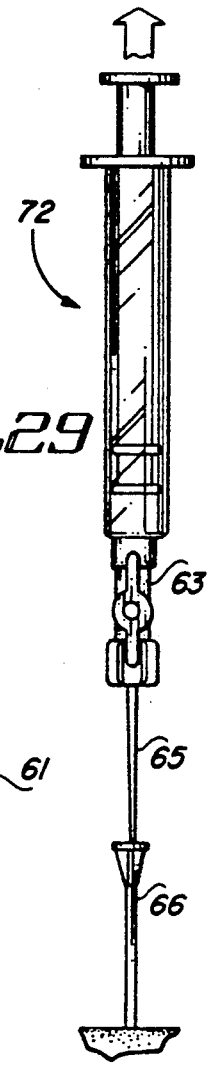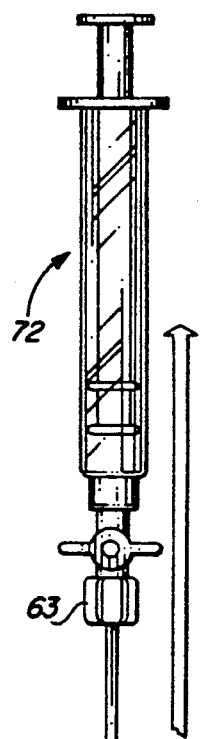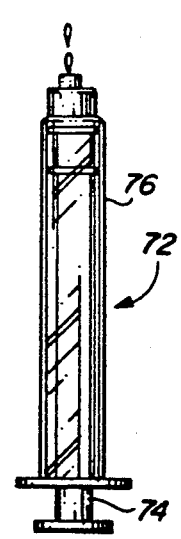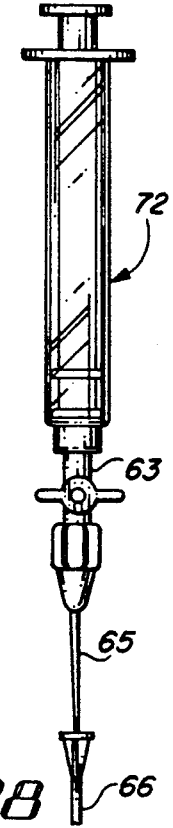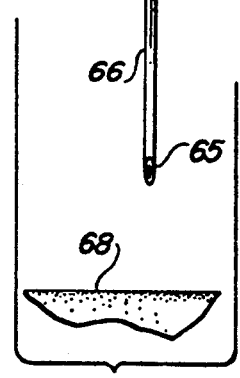

12
ASPIRATION AND REFILL KIT FOR A MEDICATION INFUSION PUMP

BACKGROUND OF THE INVENTION

1. Field of the Invention

This invention relates generally to an improved kit and related method of use for quickly and easily refilling a medication reservoir of a medication infusion pump, particularly such as an infusion pump of the type adapted for implantation into the body of a patient. More particularly, this invention relates to an improved syringe designed for use in combination with other kit components to facilitate rapid and safe refilling of the pump reservoir.

Medication infusion pumps are generally known in the art for use in delivering a selected medication to a patient in a scheduled or preprogrammed manner. In recent years, such infusion pumps have been developed in compact form adapted for implantation into the body of a patient. They are used to deliver a specific medication such as insulin to the patient in discrete (but essentially continuous) doses over an extended time period. An implanted infusion pump of this general type typically includes an internal medication reservoir which is often subjected (for safety reasons) to a storage pressure less than ambient body pressure (negative pressure) to prevent undesired leakage of the medication from the reservoir.

Other implantable pumps may use neutral or positive pressure reservoirs, although they are not deemed to be as safe as negative pressure reservoirs. Other components included in the device include a power source, a miniature pump, and associated electronic programmed control means for delivering the medication to the patient according to a prescribed schedule. For one illustrative example of an implanted or implantable medication infusion pump of this general type, see U.S. Pat. No. 4,573,994, to Fischell.

Implanted medication infusion pumps are normally equipped with an inlet port through which fluid medication can be supplied to permit periodic refilling of the pump reservoir. This inlet port is typically positioned and shaped for receiving a transcutaneous needle through which the fluid medication is supplied from outside the patient's body. Accordingly, the pump reservoir can be filled or refilled without requiring surgical removal from the patient's body, and further without requiring any other significant surgical procedure.

While implantable, refillable medication infusion pumps constitute a major step forward in reliable and convenient administration of certain medications, devices and methods for periodically refilling the pump reservoir have been relatively complex and/or difficult to use such that refilling procedures have not been optimized, particularly with negative pressure reservoir devices. More particularly, syringe implements having a standard barrel and plunger have been used in combination with an appropriate transcutaneous needle to access the pump reservoir, with plunger retraction or advancement respectively aspirating residual medication from or supplying fluid medication into the reservoir.

Unfortunately, it has often been difficult to hold such syringe implements securely and safely while applying sufficient manual force to manipulate the syringe plunger. As a result, in the past, refill procedures have required a relatively high level of skill and have proceeded at a relatively slow pace. Moreover, it has normally been required for fluid medication to be degassed immediately before injection into the pump reservoir, such that the presence of relatively costly and sophisticated degassing equipment has also been required.

The present invention provides a relatively simple and easy-to-use kit for quickly and easily delivering fluid medication to the reservoir of an implanted infusion pump, wherein the improved kit provides effective and simple means for degassing the fluid medication. Moreover, the present invention provides for rapid and safe aspiration of residual medication prior to reservoir filling. In either case, the invention provides an improved aspiration or refill syringe adapted for drawing or delivering medication without requiring concurrent manipulation of a syringe plunger.

SUMMARY OF THE INVENTION

In accordance with the invention, an improved kit is provided for use in refilling a medication reservoir within a medication infusion pump, particularly such as an implanted infusion pump adapted for programmed delivery of a selected fluid medication into the body of a patient. The kit generally comprises an improved syringe having a syringe barrel with a reciprocal plunger received therein, and a manually operable control valve at a nose end of the syringe barrel. Lock means interacting between the plunger and barrel are also provided for retaining the plunger in a retracted position subsequent to plunger retraction with the control valve closed, thereby permitting a vacuum to be drawn and maintained within the syringe barrel. This drawn vacuum permits the improved syringe to aspirate residual medication from the pump reservoir without requiring simultaneous manual plunger retraction. Alternately, the drawn vacuum permits the syringe to be used as a degassing device to degas fluid medication before injection into the pump reservoir, and then to deliver such medication without requiring simultaneous manual plunger advancement.

The plunger stem is tapered to a reduced diameter at the proximal end (the end extending from the syringe barrel) to prevent prestressing the lock means when the plunger is fully inserted into the syringe barrel (its stored position). The plunger also includes two radially outwardly-extending annular rings disposed on the outer diameter of the plunger stem near the distal end (the end inserted into the syringe barrel). These rings maintain a coaxial relationship between the plunger and the syringe barrel.

In the preferred form, the improved syringe is provided as part of a kit consisting of disposable components adapted for controlled communication between the syringe barrel and the pump reservoir. In one form, the kit is used to aspirate residual medication from the pump reservoir preparatory to pump refilling. In another form, the kit is used to refill the pump reservoir. An identical pair of the kits can be used when both aspiration and refilling are desired.

More particularly, when the kit is used to aspirate the medication reservoir of the infusion pump, the syringe plunger is retracted and locked while the control valve is maintained in a closed position to result in drawing of a vacuum within the syringe barrel. The preferred lock means comprises a lock tab carried by the syringe barrel and adapted for normal spring biased reception into a recess or groove formed on the plunger, wherein the plunger recess is positioned to receive the lock tab when the plunger is retracted. The syringe barrel is then coupled through the control valve and an appropriate aspiration needle with the pump reservoir, and the control valve is opened to permit the barrel vacuum to aspirate the pump reservoir.

Alternately, when the kit is used to refill the pump reservoir, the syringe plunger is partially retracted to draw a quantity of a selected medication into the syringe barrel. The plunger is then further retracted and locked while the control valve is maintained in a closed position, thereby drawing a vacuum within the syringe barrel for use in vacuum-degassing of the medication. The syringe barrel can then be coupled with the pump reservoir via a refill needle and the control valve opened to permit medication delivery to the pump reservoir. In the preferred system, the pump reservoir is maintained at a pressure below ambient body pressure and the barrel vacuum is released prior to connection with the pump reservoir, such that the fluid medication is vacuum-drawn into the pump reservoir. The refill device of the present invention will, however, work with a neutral or positive pressure reservoir.

Other features and advantages of the present invention will become more apparent following a detailed description of the preferred implementation of the present invention. All of the aforesaid advantages and objectives of the present invention are achieved without incurring any substantial relative disadvantage.

DESCRIPTION OF THE DRAWINGS

The advantages of the present invention are best understood with reference to the drawings, in which:

FIG. 4 is a fragmented vertical sectional view illustrating an exemplary medication infusion pump of a type adapted for in vivo placement;

FIG. 5 is an elevational view depicting initial syringe priming with a diluting solution;

FIG. 6 is an elevational view of the syringe of FIG. 5 illustrating mounting of an aspiration needle and associated control valve onto the syringe;

FIG. 7 is an elevational view similar to FIGS. 5 and 6, showing initial priming of the aspiration needle and control valve with the diluting solution;

FIG. 8 is a fragmented elevational view depicting post-priming closure of the control valve;

FIG. 10 is a fragmented elevational view illustrating engagement of a main guide needle with the infusion pump;

FIG. 12 is an enlarged fragmented sectional view depicting the aspiration and guide needles in operative association with the infusion pump;

FIG. 16 is a fragmented elevational view showing mounting of a control valve onto the refill syringe;

FIG. 19 is an elevational view showing retraction of a syringe plunger to draw a vacuum within the syringe barrel, and subsequent shaking of the syringe to degas the medication therein;

FIG. 20 is a fragmented elevational view showing mounting of a refill needle onto the refill syringe;

FIG. 21 is an elevational view depicting priming of the refill needle mounted onto the syringe;

FIG. 22 is a fragmented elevational view illustrating closure of the control valve subsequent to priming of the refill needle;

FIG. 23 is an elevational view showing insertion of the refill needle on the syringe through the main guide needle and associated operation of the control valve to deliver the medication to the infusion pump for refilling thereof;

FIG. 24 is a fragmented elevational view depicting closure of the control valve at the conclusion of a refilling step;

FIG. 25 is a fragmented elevational view depicting removal of the refill syringe from the closed control valve;

FIG. 26 is an elevational view illustrating priming of an auxiliary syringe with a small amount of diluting solution;

FIG. 27 is an elevational view showing purge of air from the auxiliary syringe subsequent to removal of a fill needle therefrom;

FIG. 28 is an elevational view illustrating mounting of the auxiliary syringe onto the closed control valve;

FIG. 29 is an elevational view showing use of the auxiliary syringe to draw a small quantity of the fluid medication from the infusion pump to maintain the medication therein under negative pressure; and FIG. 30 is an elevational view illustrating withdrawal of the auxiliary syringe and control valve and related components as a unit from the patient.

DETAILED DESCRIPTION OF THE PREFERRED EMBODIMENT

Figure 1:
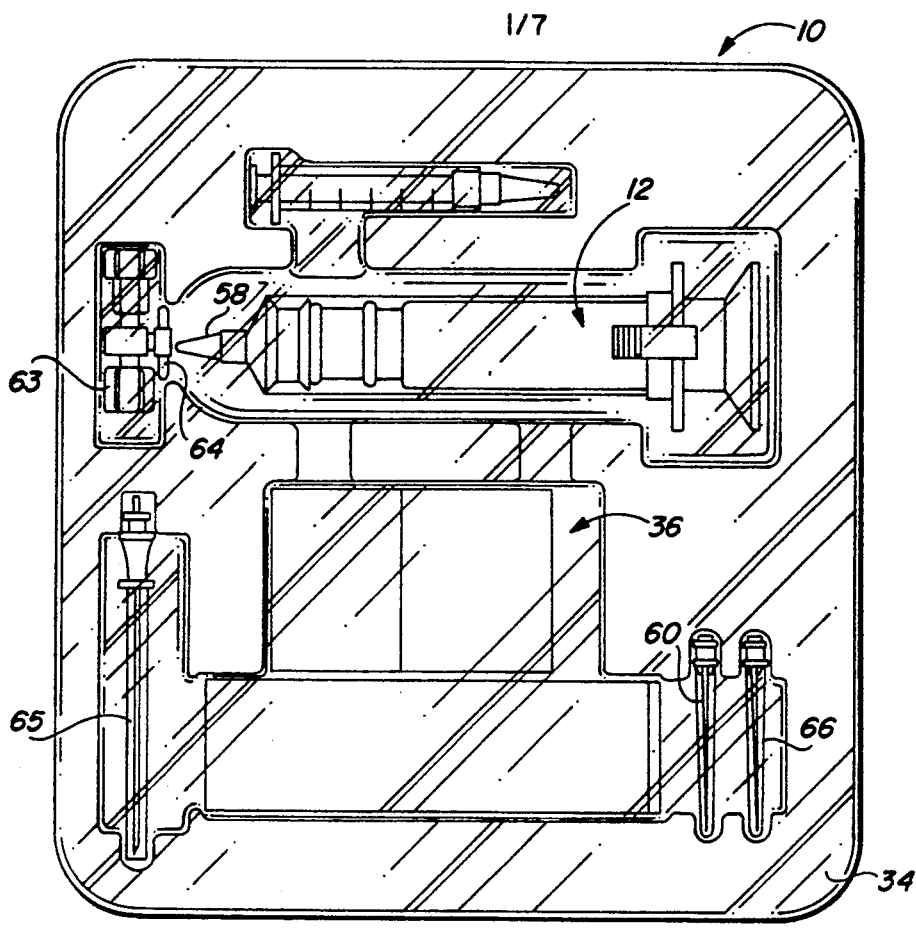
FIG. 1 is a plan view illustrating an aspiration or refill kit for use with an implanted medication infusion pump, in accordance with the novel features of the invention.

As shown in the exemplary drawings, a kit referred to generally by the reference numeral 10 in FIG. 1 is provided for use in refilling a medication infusion pump of the general type adapted for direct implantation into the body of a patient. The kit 10 includes an improved syringe 12 in combination with other components for quick and easy access to and refilling of an implanted infusion pump. Moreover, if desired, the kit 10 can be used for facilitated aspiration of residual medication from an implanted pump, preparatory to refilling thereof.

The improved kit 10 of the present invention is designed for use with medication infusion pumps of the general type shown and described by way of illustration in U.S. Pat. No. 4,573,994, the disclosure of which is incorporated by reference herein. More particularly, as shown in FIG. 4, such infusion pumps 14 have included an hermetically sealed housing 16 adapted for implantation into the body of a patient and having an internal reservoir 18 for receiving and storing a supply of a selected medication, such as insulin for a diabetic patient. In a typical pump of this type, a titanium bellows-type reservoir may be used instead of the reservoir 18 shown in FIG. 4.

The housing 16 further contains a miniature pump (not shown) and associated electronic control circuitry 20 for periodically operating the pump to deliver a dose of the medication from the reservoir 18 to the patient. The control circuitry 20 is preprogrammed to deliver the medication in accordance with individual patient need. As is known in the art, the illustrative pump includes a negative pressure Freon chamber 22 filled with an appropriate vapor or liquid such as Freon 113 for maintaining the medication within the reservoir 18 at a pressure level below ambient body pressure. Other pumps have neutral or positive pressure, and the device of the present invention could also be used with them, although less advantageously.

The illustrative infusion pump 14 includes an inlet port 24 at one side of the housing 16 to permit periodic refilling of the pump reservoir 18 without requiring surgical access to the implanted pump. More particularly, the inlet port 24 as shown in FIG. 4 has a generally conical or funnelled geometry which tapers from a relatively large outboard end to a narrow inboard or apex end disposed adjacent to an underlying resilient and self-sealing septum 26. A suitable hypodermic needle (not shown in FIG. 4) may be inserted transcutaneously into the inlet port 24, with the funnelled shape being defined by a hard surface to guide the pointed needle tip downwardly to pierce the septum 26.

The tip of the needle may thus be inserted into a small antechamber 28 underlying the septum for purposes of injecting fluid medication into the antechamber 28. The antechamber 28 communicates in turn with the pump reservoir 18 via a suitable safety valve 30 and an associated conduit 32. Alternately, a valve actuated by the needle may be utilized. Such a valve is shown in U.S. Pat. No. 4,573,994, to Fischell et al. (jointly owned by the assignee of the present invention), which patent is hereby incorporated herein by reference.

The kit 10 of the present invention includes the improved syringe 12 in association with appropriate hypodermic needles for use in transcutaneously accessing the pump reservoir 18 via the antechamber 28. In this regard, the syringe 12 and associated kit components are desirably provided as a prepackaged and presterilized unit as shown in FIG. 1 to include a vacuum formed tray 34 with an overlying peel-off cover. This kit 10 can be used either to deliver fluid medication to the pump reservoir 18, or to aspirate residual medication from the reservoir as typically desired in advance of a refill procedure. When aspiration and refilling steps are desired in sequence, it will be understood that a pair of the kits 10 as viewed in FIG. 1 will be used. Moreover, in addition to the various kit components to be described in detail herein, it will be understood that the kit 10 will normally include appropriate transcutaneous injection site preparation, drapery, and/or dressing materials referred to generally in FIG. 1 by the reference numeral 36.

Figure 3:
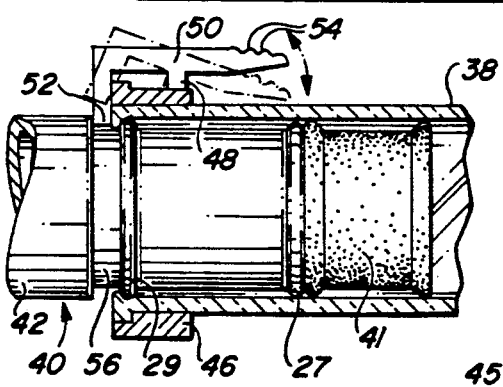
FIG. 3 is an enlarged and fragmented longitudinal sectional view of a portion of the syringe, taken generally on the line 3—3 of FIG. 2.
Figure 2:
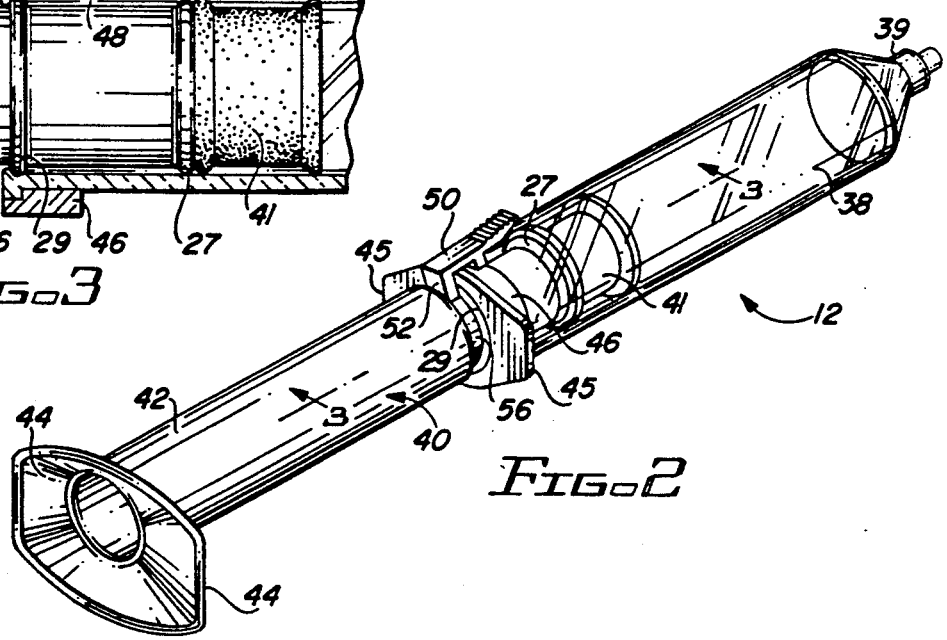
FIG. 2 is an enlarged perspective view of an aspiration or refill syringe forming a portion of the kit of the invention.

The improved syringe 12 is shown in more detail in FIGS. 2 and 3. More specifically, the syringe 12 comprises a relatively large, hollow and open-ended syringe barrel 38 having a male luer lock fitting 39 formed at a nose end thereof and defining a conventional barrel port for intake and discharge of fluid from the barrel interior. A syringe plunger 40 includes a resilient piston 41 slideably fitted into the barrel 38. The piston 41 is mounted at the distal end of an elongated plunger stem 42, the proximal end of which protrudes outwardly from the rear end of the barrel 38.

The distal end of the plunger 40 includes two radially outwardly extending annular rings 27 and 29, which are spaced apart as best shown in FIG. 3. The rings 27 and 29, which have an outer diameter closely fitting the inner diameter of the barrel 38, function to retain the plunger 40 in a coaxial relationship with the barrel 38. Thus, the plunger 40 is prevented from wobbling in the barrel 38, which wobbling could have an adverse effect on the seal of the piston 41 in the barrel 38.

In addition, the plunger stem 42 is tapped to a smaller diameter at the distal end thereof. This smaller diameter prevents prestressing of the plunger locking mechanism, which will be discussed below. The outermost end of the plunger stem 42 terminates in a pair of enlarged projecting wings 44 which may be utilized together with similar wings 45 on the rear end of the barrel 38 to facilitate manual grasping to advance and retract the plunger 40, as desired.

In accordance with one primary aspect of the invention, lock means are provided for releasably locking or retaining the syringe plunger 40 in a retracted position within the syringe barrel 38. The preferred lock means shown in FIGS. 2 and 3 comprises a cylindrical collar 46 fitted slideably and relatively closely about the cylindrical syringe barrel 38 at a position adjacent to the outwardly projecting wings 45. This collar 46, which conveniently may be formed from molded plastic, is joined to an outwardly projecting fulcrum member 48 connected in turn to an approximate midpoint on a lock lever 50 extending longitudinally a short distance along the syringe barrel 38.

One end of the lock lever 50 defines an inwardly directed lock tab 52 which overhangs the rearmost end of the syringe barrel 38, whereas the opposite end of the lock lever includes transversely extending serrations 54 to facilitate fingertip depression thereon. The fulcrum member 48 provides sufficient resilient to permit pivotal movement of the lever 50 for purposes of lifting the lock tab 52 to the dotted line position as viewed in FIG. 3, with the natural resiliency of the fulcrum member 48 urging the tab 52 to return to the normal solid line position when the lever is released.

When the plunger 40 is fully inserted into the barrel 38 (as in the storage position shown in FIG. 1), the tab 52 will be allowed to return to the normal solid line position. However, as the plunger 40 is retracted from the barrel 38, the tab 52 will be urged radially outwardly into the dotted line position. Importantly, when the syringe plunger 40 is moved to a retracted position as illustrated in FIGS. 2 and 3, the lock tab 52 is biased to seat within a circumferential recess or groove 56 in the plunger stem 42 to lock and retain the plunger in the retracted position until subsequent depression of the serrated end 54 of the lock lever 50 to lift the tab 52 from the lock groove 56.

FIGS. 5–14 illustrate a sequence of steps using the kit 10 of the present invention to aspirate residual medication from the reservoir 18 of an implanted infusion pump 14. Similarly, FIGS. 15–30 illustrate a preferred sequence of method steps using the kit 10 to refill the pump reservoir 18. These steps will be discussed with reference to a negative pressure reservoir device, although those skilled in the art will understand that the present invention is also applicable to neutral or positive pressure reservoir devices.

More particularly, with reference to FIG. 5, the improved syringe 12 is initially primed with a suitable liquid such as a conventional saline based diluting solution or the like. This priming step is performed by removing a protective cap 58 (FIG. 1) form the male luer lock fitting 39 at the nose end of the syringe barrel 38 and connecting a hypodermic needle 60 (which has a female luer lock fitting) thereto. The needle 60 can then be used to pierce the self-sealing stopper of a suitable solution container 61 (FIG. 5), after which the syringe plunger 40 is retracted a short distance in the direction of arrow 62 to draw a small quantity of the diluting solution into the syringe barrel.

Subsequent to the initial priming step, the needle 60 is removed from the syringe barrel 38 and suitably discarded, as illustrated in FIG. 6. A stopcock type control valve 63 (having a female luer fitting on one end thereof and a male luer fitting on the other end thereof) is then mounted (using its female luer fitting) onto the nose end of the syringe barrel. This control valve 63 includes a manually movable valve handle 64 adapted for movement between open and closed positions for respectively opening and closing an internal valve member (not shown). A relatively long and small gauge aspiration needle 65 (having a female luer fitting) is next mounted onto the outboard end of the control valve 63 and the valve handle 64 is placed in the open position. The syringe plunger 40 is advanced, as viewed in FIG. 7, while the syringe 12 is held in an inverted orientation to purge air from the syringe barrel 38, the control valve 63, and the aspiration needle 65, such that these components are fully primed and only a small quantity of the diluting solution remains within the nose end of the syringe barrel. The control valve 63 is then closed by appropriate movement of the valve handle 64, as viewed in FIG. 8.

Figure 9:
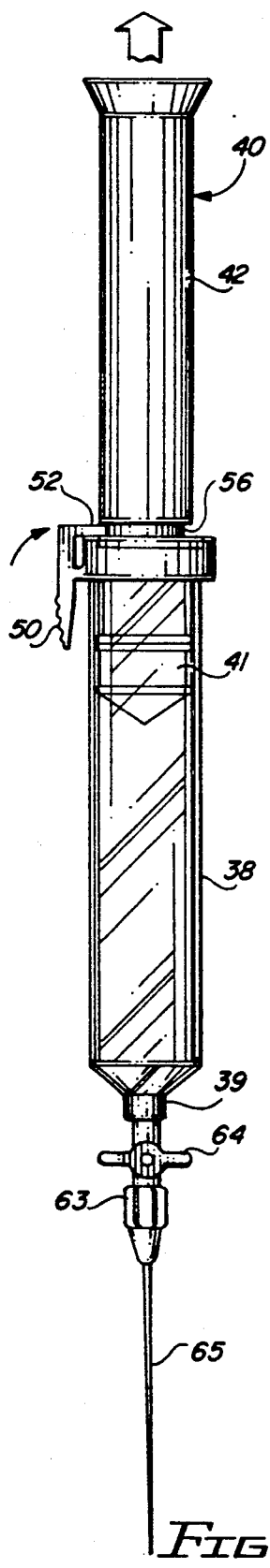
FIG. 9 is an elevational view of the syringe showing retraction of a syringe plunger to draw a vacuum within the syringe barrel.

With the control valve 63 in the closed position, the syringe plunger 40 is manually moved to the retracted position, as shown in FIG. 9. That is, the plunger 40 is retracted until the lock groove 56 on the stem 42 aligns with the lock tab 52 on the lever 50, at which time the natural resiliency of the fulcrum member 48 causes the tab 52 to displace into the lock groove. Such displacement of the tab 52 effectively locks the plunger against further advancing or retracting movement. Importantly, as a result of this plunger retraction and positional locking, a significant vacuum is drawn and maintained within the syringe barrel.

As shown in FIG. 10, an introducer or guide needle 66 which may be similar or identical to the priming needle 60 is introduced through the skin 68 of the patient into the inlet port 24 of the implanted infusion pump 14. In this regard, it will be understood that the pump 14 is normally implanted at a convenient location for relatively easy palpated identification of the inlet port 24 for refilling purposes. The guide needle 66 pierces the skin 68 and passes into the conical inlet port 24 which guides the needle 66 further downwardly toward the septum 26. However, the gauge of the guide needle 66 is chosen to prevent passage of the needle tip into contact with the septum. Instead, the apex region of the inlet port 24 obstructs further downward passage of the needle 66 at a location spaced slightly above the septum 26.

Figure 11:
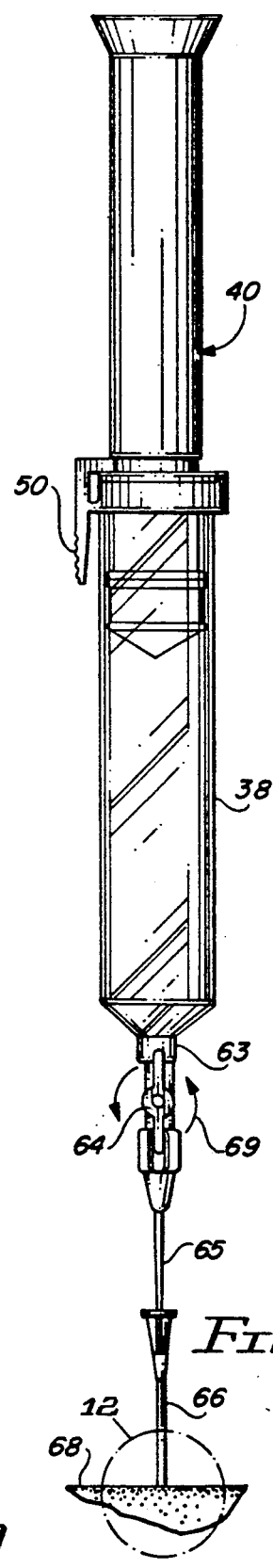
FIG. 11 is an elevational view showing insertion of the aspiration needle through the main guide needle.
Figure 13:
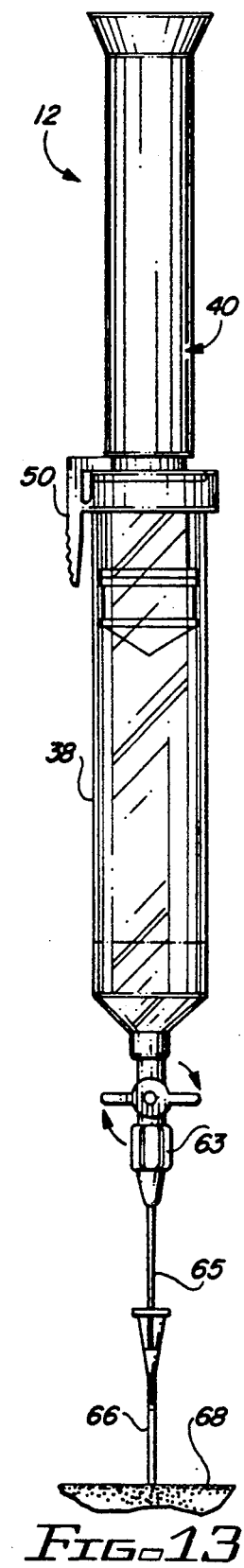
FIG. 13 is an elevational view showing opening of the control valve to permit vacuum-draw aspiration of residual medication from the infusion pump.

With the guide needle 66 in place, the aspiration needle 65 mounted on the syringe 12 is slideably fitted through the guide needle 66 to pierce the septum 26 and thereby gain access to the antechamber 28 below the septum, as shown in FIGS. 11 and 12. This step is performed while maintaining the control valve 63 in a closed condition. However, as depicted by arrow 69 in FIG. 11, the handle 64 on the control valve 63 is turned to the open position subsequent to seating of the aspiration needle 65 into the pump antechamber 28. As a result, the vacuum drawn previously within the syringe barrel 38 is coupled to the pump reservoir 18 via the antechamber 28, such that the syringe vacuum effectively overrides the reservoir vacuum to aspirate any residual medication from the reservoir 18. This aspiration step is performed without requiring the syringe plunger 40 to be advanced or retracted relative to the syringe barrel during the time of access with the reservoir.

Figure 14:
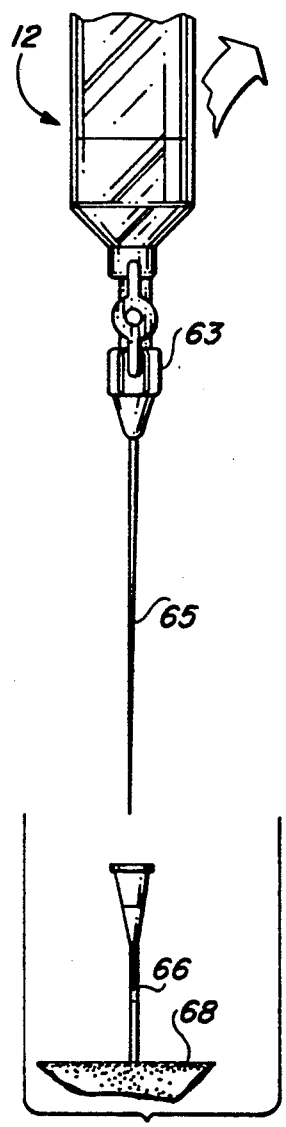
FIG. 14 is a fragmented elevational view depicting withdrawal of the aspiration syringe from the main guide needle at the conclusion of pump aspiration.

When the aspiration step is completed as indicated visually by cessation of medication flow into the typically transparent syringe barrel 38, the control valve 63 is closed (FIG. 13) to uncouple the reservoir 18 from the syringe 12. The syringe with connected control valve 63 and the aspiration needle 65 are then withdrawn as a unit from the guide needle 66 (FIG. 14). The aspirated medication may be analyzed, if desired, and the syringe 12 is normally discarded. Importantly, the guide needle 66 may remain in place for subsequent use in refilling of the reservoir 18, as will be described with respect to FIGS. 15–30.

To refill the pump reservoir, a second syringe 12 taken from a second kit 10 identical to that depicted in FIG. 1 is utilized. As viewed, in FIG. 15, the hypodermic needle 60 of the second kit is mounted onto the nose end of the syringe barrel 38, and the needle 60 is oriented to pierce a self-sealing stopper of an inverted container 70 having a supply of a selected medication, such as insulin. The syringe plunger 40 is retracted through a partial stroke to partially fill the barrel 38 with the medication. The needle 60 is than removed and discarded, and a fresh control valve 63 having a movable valve handle 64 is mounted onto the syringe barrel, as shown in FIG. 16.

Figure 18:
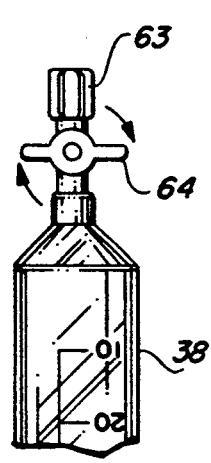
FIG. 18 is a fragmented elevational view depicting closure of the control valve on the syringe subsequent to air purge.
Figure 17:
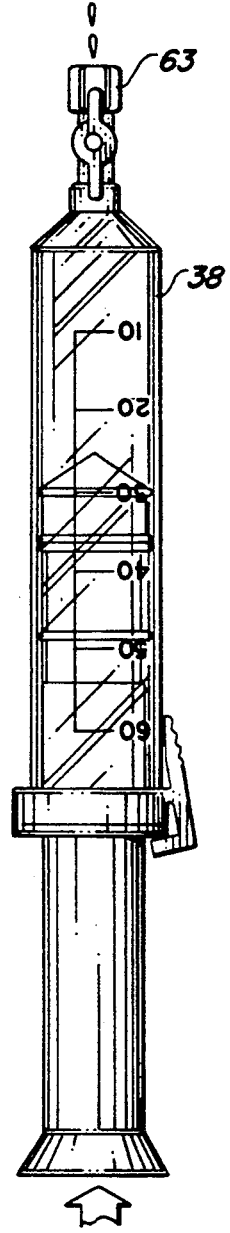
FIG. 17 is an elevational view illustrating purging of air from within the barrel of the refill syringe.
Figure 15:
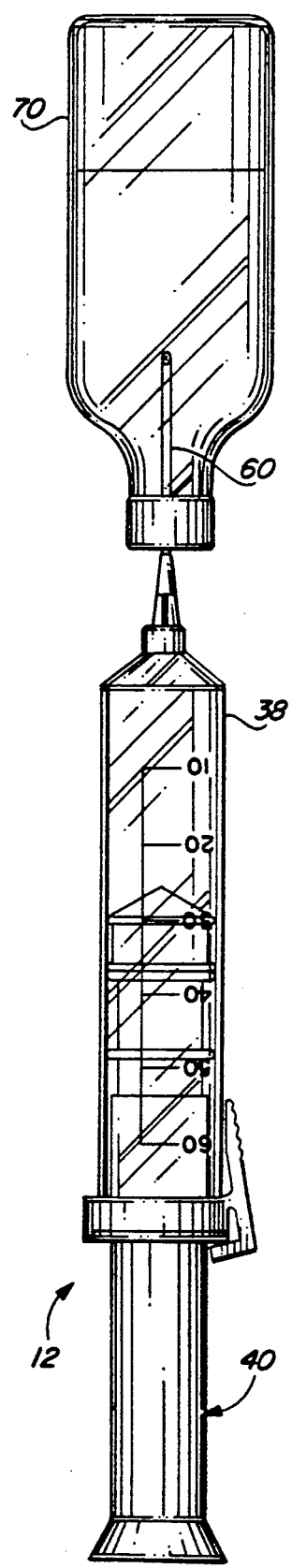
FIG. 15 is an elevational view showing the syringe for use in refilling of the infusion pump with fluid medication, depicting partial filling of the syringe with a selected medication.

With the control valve handle 64 in an open position and the syringe 12 held in an inverted orientation, the syringe plunger 40 is advanced through a short stroke sufficient to purge air from the syringe barrel and the control valve (FIG. 17). The control valve handle 64 is then switched to the closed position as shown in FIG. 18, and the plunger 40 is retracted to the locked position with the lock tab 52 seated within the plunger groove 56 (FIG. 19). Such plunger retraction draws a significant vacuum within the syringe barrel 38. The entire syringe 12 can then be shaken vigorously for a short time interval, with the barrel vacuum serving to effectively degas the fluid medication.

Subsequent to the degassing step, a refill needle 65 (having a female luer fitting) corresponding with the aspiration needle 65 of FIG. 1 is mounted onto the control valve 63 (FIG. 20), and the control valve handle 64 is moved to the open position (FIG. 21). The plunger 40 is then released or unlocked by depression of the lock lever 50 to permit plunger advance sufficiently to prime the needle 65 with the fluid medication. The control valve 63 is re-closed (FIG. 22), and the refill needle 65 is inserted through the guide needle 66 (FIG. 23) for piercing the septum 26 and accessing the pump reservoir 18 via the antechamber 28, as described previously and as best shown in FIG. 12.

With the refill needle 65 in flow communication with the pump reservoir 18, the control valve 63 is opened (FIG. 23). In this configuration, in the preferred system arrangement, the pump reservoir which is maintained under negative pressure by the Freon chamber 22 (FIG. 4) vacuum-draws the medication from the syringe barrel 38 into the pump reservoir. As a result, the reservoir 18 fills with medication without requiring the plunger 40 to be manually displaced by attending medical personnel while the refill needle 65 is within the antechamber 28. Alternately, for infusion pumps having a positive pressure internal reservoir, advancing motion of the plunger 40 will be required to deliver the fluid medication. When the reservoir 18 reaches a substantially filled condition as indicted by a half in vacuum-draw movement of the plunger 40 when a negative pressure pump reservoir is used, the control valve 63 is closed (FIG. 24) and the syringe barrel 38 is separated from the control valve 63 for disposal (FIG. 25).

When the reservoir 18 reaches the substantially filled condition, the reservoir pressure will approach or equal ambient body pressure. However, it is desirable to impose a negative pressure on the reservoir promptly after refilling, thereby preventing an inadvertent positive pressure condition in the event that the patient encounters significant altitude changes. In this regard, the kit 10 includes an auxiliary syringe 72 (FIG. 26) which is adapted for initial priming with a diluting solution, and subsequent purge of air following needle discard by advancing a plunger 74 into a syringe barrel 76 (FIG. 27). The auxiliary syringe 72 is then coupled with the still-closed control valve 63 which remains on the refill needle 65 in communication with the implanted pump (FIG. 28). The control valve 63 is then opened and the auxiliary syringe plunger 74 is retracted to withdraw a small quantity of the medication from the pump reservoir (FIG. 29), and thereby reimpose a significant negative pressure on the reservoir by action of the Freon chamber 22 (FIG. 4). The control valve 63 is closed again, and the kit components including the auxiliary syringe 72, control valve 63, and the needles 65 and 66 are withdrawn from the patient as a unit (FIG. 30).

Accordingly, the aspiration and refill kit 10 of the present invention permits relatively rapid refill and/or preliminary aspiration of the medication within the reservoir of an implanted infusion pump. The aspiration and/or refill steps can be performed quickly and easily, with each step being of a relatively simple and safe nature. In the preferred form for use with a negative pressure pump reservoir, aspiration and refilling can proceed without requiring manually forced displacement of a syringe plunger while the syringe is engaged with the implanted pump. Moreover, the improved syringe 12 provides a simple and inexpensive device for degassing medication prior to introduction of the medication into the implanted pump.

Although an exemplary embodiment of the present invention has been shown and described, it will be apparent to those having ordinary skill in the art that a wide variety of changes, modifications, alterations, or improvements to the invention as described herein may be made, none of which depart from the spirit of the present invention. All such changes, modifications, and alterations should therefore be seen as within the scope of the present invention.

What is claimed is:

1. A kit for use in refilling an implantable medication infusion pump having an internal reservoir for receiving and storing a selected medication, an inlet port containing a self-sealing septum, an interior portion of the inlet port being in fluid communication with the internal reservoir, said kit comprising:

a syringe having a hollow syringe barrel with a nose end and an open rear end, and further including a reciprocal plunger received slideably within said open rear end of said barrel;

a control valve adapted for mounting onto said nose end of said syringe barrel and including means for selectively opening and closing said control valve;

lock means having a first element mounted on said syringe barrel, said first element of said lock means for releasable engagement with a second element of said lock means disposed on said plunger, said lock means for releasably locking said plunger in a retracted position within said barrel in which longitudinal movement of said plunger is completely inhibited, whereby a significant vacuum may be drawn and maintained within said barrel by retracting said plunger to said retracted position while said control valve is closed; and needle means adapted for mounting onto said control valve for piercing the pump septum to access the inlet port.

2. A kit as defined in claim 1, further comprising:

a guide needle adapted for insertion at least partially into the inlet port without piercing the self-sealing septum, said needle means for mounting onto said control valve being slideably insertable through said guide needle and the self-sealing septum into fluid communication with the internal reservoir.

3. A kit as defined in claim 1, wherein said means for opening and closing said control valve comprises:

means for allowing said control valve to be opened when said needle means is in fluid communication with the internal reservoir such that the vacuum within the syringe barrel aspirates residual medication from the internal reservoir.

4. A kit as defined in claim 1, wherein said plunger has an inserted position in which said plunger is fully inserted into said syringe barrel and an intermediate position between said inserted position and said retracted position, said syringe being adapted to draw in a first volume of the medication when said plunger is moved from said inserted position to said intermediate position, said plunger thereafter being adapted for movement to said retracted position with said control valve closed to draw a significant vacuum within the syringe barrel to degas the medication, said syringe displacing a second volume therein when said plunger is in said retracted position, said second volume being sufficiently larger than said first volume to allow the medication to be satisfactorily degassed.

5. A kit as defined in claim 4, wherein said syringe barrel and said plunger are arranged and configured to allow said plunger to be drawn into said syringe barrel by the negative pressure of an internal reservoir in a pump having a negative pressure reservoir.

6. A kit as defined in claim 1, wherein said syringe plunger comprises:
- a piston adapted for reciprocal motion within said syringe barrel in sealing fashion; and
- a plunger stem connected to said piston and extending outwardly from said open rear end of said syringe barrel.

7. A kit as defined in claim 6, wherein said second element of said lock means comprises:
- a recess formed in said plunger stem near a forward end thereof at a position for exposure at said rear end of said barrel when said plunger is moved to said retracted position; and wherein said first element of said lock means comprises:
- a lock tab mounted on said barrel for biased movement into said recess when said plunger is moved to said retracted position.

8. A kit as defined in claim 7, wherein said lock tab is formed at one end of a lock lever mounted pivotally onto said barrel.

9. A kit as defined in claim 8, wherein said lock lever is supported on a fulcrum member projecting outwardly from a collar adapted for slidable mounting onto said barrel, said lock lever and said fulcrum member and said collar being integrally formed.

10. A kit as defined in claim 6, additionally comprising:
- means for retaining said plunger stem in a coaxial relationship with said syringe barrel.

11. A kit as defined in claim 10, wherein said retaining means comprises:
- a pair of spaced-apart, annular rings mounted on and extending radially outwardly from said plunger stem near said forward end thereof.

12. A kit as defined in claim 1, wherein said syringe barrel includes a male luer lock fitting at said nose end thereof, and wherein said control valve includes a female luer lock fitting for mating with said male luer lock fitting on said syringe barrel.

13. A kit as defined in claim 12, wherein said control valve also includes a male luer lock fitting for mating with said needle means.

14. A syringe assembly for use in aspirating and refilling a medication reservoir of an implanted medication infusion pump, said syringe assembly comprising:
- a hollow syringe barrel having a first connector fitting at a nose end thereof and defining a barrel port for intake and discharge of fluid from the interior of said barrel, said barrel further defining an open rear end;
- a syringe plunger having a piston slideably received into said barrel rear end, and a plunger stem connected to said piston and projecting outwardly from said barrel rear end;
- a control valve having a second connector fitting which is removably mounted onto said first connector fitting, said control valve including means for selectively opening and closing said valve;
- said plunger being movable within said barrel between an advanced position to a retracted position with said control valve closed to draw a substantial vacuum within said syringe barrel; and
- lock means cooperating between said barrel and plunger for retaining said plunger in said retracted position in which longitudinal movement of said plunger is completely inhibited.

15. A syringe assembly as defined in claim 14, wherein said lock means comprises:
- a recess formed in said plunger near a forward end thereof at a position for exposure at said rear end of said barrel when said plunger is moved to said retracted position; and
- a lock tab on said barrel for movement into said recess when said plunger is moved to said retracted position.

16. A syringe assembly as defined in claim 15, wherein said lock tab comprises:
- means for urging said tab toward reception into said recess when said plunger is in said retracted position; and
- means for manually withdrawing said tab from said recess.

17. A syringe assembly as defined in claim 15, wherein said lock tab is formed at one end of a lock lever mounted pivotally onto said barrel.

18. A syringe assembly as defined in claim 17, wherein said lock lever is supported on a fulcrum member projecting outwardly from a collar adapted for slidable mounting onto said barrel, said lock lever and said fulcrum member and said collar being integrally formed.

19. A kit for aspirating residual medication from a medication reservoir within an implantable medication infusion pump having an inlet port including a self-sealing septum, said kit comprising:
- a syringe including a hollow syringe barrel having a connector fitting at a nose end thereof and defining a barrel port for intake and discharge of fluid from the interior of said barrel, said barrel further defining an open rear end, said syringe further including a syringe younger having a piston slideably received into said barrel rear end, and a plunger stem connected to said piston and projecting outwardly from said barrel rear end;
- a control valve removably mounted onto said connector fitting, said control valve including means for selectively opening and closing said valve, said plunger being movable within said barrel between an advanced position to a retracted position with said control valve closed to draw a substantial vacuum within said syringe barrel;
- lock means cooperating between said barrel and plunger for retaining said plunger in said retracted position in which longitudinal movement of said plunger is completely inhibited; and
- an aspiration needle adapted for mounting onto said control valve and for piercing the pump septum to access the pump reservoir, said means for opening and closing said control valve being movable to open said control valve, thereby communicating the vacuum within said syringe barrel with the pump reservoir to aspirate residual medication within the reservoir into said syringe barrel.

20. A kit for refilling a medication reservoir within an implantable medication infusion pump having an inlet port including a self-sealing septum, said kit comprising:
- a syringe including a hollow syringe barrel having a connector fitting at a nose end thereof and defining a barrel port for intake and discharge of fluid from the interior of said barrel, said barrel further defining an open rear end, said syringe further including a syringe plunger having a piston slideably received into said barrel rear end, and a plunger stem connected to said piston and projecting outwardly from said barrel rear end;

a control valve removably mounted onto said connector fitting, said control valve including means for selectively opening and closing said valve, said plunger being movable within said syringe barrel with said control valve open to draw in a quantity of a selected medication to partially fill said barrel, said plunger being further movable within said barrel with said control valve closed and in a direction toward a retracted position to draw a substantial vacuum within said syringe barrel to degree the medication therein;

lock means cooperating between said barrel and plunger for retaining said plunger in said retracted position during degassing of the medication, said lock means completely inhibiting longitudinal movement of said plunger; and a refill needle adapted for mounting onto said control valve and for piercing the pump septum to access the pump reservoir, said means for opening and closing said control valve being movable to open said control valve thereby communicating the interior of said syringe barrel with the pump reservoir to permit refilling of the pump reservoir with said selected medication.

21. A kit for aspirating and refilling an internal medication reservoir of an implantable medication infusion pump having an inlet port including a self-sealing septum, said kit comprising:

a first syringe assembly comprising:

a hollow syringe barrel having a connector fitting at a nose end thereof and defining a barrel port for intake and discharge of fluid from the interior of said barrel, said barrel further defining an open rear end;

a syringe plunger having a piston slideably received into said barrel rear end, and a plunger stem connected to said piston and projecting outwardly from said barrel rear end;

a control valve removably mounted onto said connector fitting, said control valve including means for selectively opening and closing said valve, said plunger being movable within said barrel between an advanced position to a retracted position with said control valve closed to draw a substantial vacuum within said syringe barrel;

lock means cooperating between said barrel and plunger for retaining said plunger in said retracted position; and an aspiration needle adapted for mounting onto said control valve and for piercing the pump septum to access the pump reservoir, said means for opening and closing said control valve being movable to open said control valve thereby communicating the vacuum within said syringe barrel with the pump reservoir to aspirate residual medication within the reservoir into said syringe barrel;

a guide needle adapted for insertion at least partially into said pump inlet port without piercing said pump septum, said aspiration needle being sized to fit slideably through said guide needle to pierce said pump septum; and a second syringe assembly comprising:

a hollow syringe barrel having a connector fitting at a nose end thereof and defining a barrel port for intake and discharge of fluid from the interior of said barrel, said barrel further defining an open rear end;

a syringe plunger having a piston slideably received into said barrel rear end, and a plunger stem connected to said piston and projecting outwardly from said barrel rear end;

a control valve removably mounted onto said connector fitting, said control valve including means for selectively opening and closing said valve, said plunger being movable within said syringe barrel with said control valve open to draw in a quantity of a selected medication to partially fill said barrel, said plunger being further movable within said barrel with said control valve closed and in a direction toward a retracted position to draw a substantial vacuum within said syringe barrel to degas the medication therein;

lock means cooperating between said barrel and plunger for retaining said plunger in said retracted position during degassing of the medication; and a refill needle adapted for mounting onto said control valve and for piercing the pump septum to access the pump reservoir, said means for opening and closing said control valve being movable to open said control valve, thereby communicating the interior of said syringe barrel with the pump reservoir to permit refilling of the pump reservoir with said selected medication, said refill needle being sized to fit slideably through said guide needle to pierce said pump septum.

22. A kit as defined in claim 21 further comprising:

an auxiliary syringe including needle means for piercing said septum and adapted to withdraw a small quantity of the medication from said pump reservoir after the pump reservoir is filled.

* * * * *